United States Patent [19]

Bombardelli et al.

[11] Patent Number: 5,043,323

[45] Date of Patent: Aug. 27, 1991

[54] COMPLEX COMPOUNDS OF BIOFLAVONOIDS WITH PHOSPHOLIPIDS, THEIR PREPARATION AND USE, AND PHARMACEUTICAL AND COSMETIC COMPOSITIONS CONTAINING THEM

[75] Inventors: Ezio Bombardelli; Gian F. Patri, both of Milan, Italy

[73] Assignee: Indena S.P.A., Milan, Italy

[21] Appl. No.: 143,470

[22] Filed: Jan. 12, 1988

[30] Foreign Application Priority Data

Jan. 14, 1987 [IT]   Italy .................................. 19081 A/87

[51] Int. Cl.[5] ..................... A61K 31/70; A61K 31/685
[52] U.S. Cl. ....................................... 514/25; 514/78; 514/844; 536/8
[58] Field of Search ............... 514/25, 78, 844; 536/8; 260/403

[56] References Cited

U.S. PATENT DOCUMENTS

4,358,442  11/1982  Wirtz-Peitz et al. .................. 514/78
4,769,508   8/1988  Gabetta et al. ........................ 514/78

FOREIGN PATENT DOCUMENTS

161445  10/1985  European Pat. Off. .............. 514/78
1152632  7/1986  Japan ..................................... 514/78

*Primary Examiner*—John W. Rollins
*Attorney, Agent, or Firm*—Bucknam and Archer

[57] ABSTRACT

Complex compounds of flavonoids with phospholipids, characterized by high lipophilia and improved bioavailability and therapeutic properties as compared with free, not complexed flavonoids. The complex compounds of the invention are suitable for use as the active principle in pharmaceutical and cosmetic compositions.

18 Claims, No Drawings

COMPLEX COMPOUNDS OF BIOFLAVONOIDS WITH PHOSPHOLIPIDS, THEIR PREPARATION AND USE, AND PHARMACEUTICAL AND COSMETIC COMPOSITIONS CONTAINING THEM

This invention is relating to complex compounds combining flavonoids with phospholipids, to a process for their preparation and to pharmaceutical and cosmetic compositions containing them.

The invention also concerns a process of obtaining flavonoids from plants which contain them.

Flavonoids, a class of substances very widely distributed in the vegetal kingdom, comprise various subclasses such as the flavans, flavanones, flavones, anthocyanins, etc . . .

The term "flavonoids" as used herein comprises all of the subclasses mentioned above.

The same flavonoids may moreover be in a monomer, dimer or oligomeric form, of up to 8 base units, and may be in a free or glycosidic form, wherein one or more hydroxyl groups are involved in glycosidic linkages with one or more saccharide units.

Flavonoids are known to possess a number of recognized and investigated pharmacological properties among which are the anti-inflammatory, antispasmodic, antihistaminic, peripheral vasodilatory, platelet antiaggregating, vasoprotector in terms of altered capillary fragility and permeability, and antiallergic properties which are in connection with, on the one hand, their antioxidant activity as free radical scavengers, and, on the other hand, the interference with many enzyme systems (phosphodiesterase, lipooxygenase, cyclooxygenase, aldosereductase, proteinkinase, histidine-decarboxylase).

Some Authors (E. Middleton, J. Tips 5, 335-338, 1984) in view of the wide range of activity of flavonoids and the capability thereof of modulating various physiological processes, have even formulated the hypothesis that flavonoids are semi-essential factors for human beings who daily take in small doses of flavonoids through their normal diet.

As a result, many therapeutic applications for flavonoids or the plant extracts containing them, have been devised and are known: however, a severe limitation exists and is imputable to the poor or very poor absorption of these active constituents when administered per os, or by topical application. The reasons for this poor absorption are partly due to a bacterial degradation of the phenol moiety of the molecule and a complex formation with other substances present in the gastrointestinal tract thus preventing them from being absorbed.

The therapeutic effect of flavonoids subsequent to parenteral administration shows, on the other hand, how the activity of these compounds is bound to their concentration in the plasma or the target organ or -tissue. The oral or topical administration of flavonoids does not permit effective concentration to be achieved on all occasions.

On the contrary, the compounds of flavonoids with phospholipids, subject of the invention, thanks to their lipophile character, are perfectly absorbed through oral admnistration and increase the therapeutic effectiveness of the flavonoids both by oral and parenteral or topical admnistration.

The phospholipids that are useful to this invention may be either vegetable or synthetic in nature, with acyl residues being the same or different, as shown by the formula:

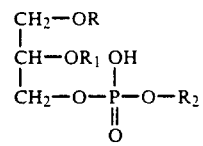

wherein R and $R_1$, that are the same or different, are mostly acyl residues of the palmitic, stearic, oleic, linoleic, linolenic acids while $R_2$ is the residue of choline, ethanolamine or serine. Particularly preferred phospholipids for use in cosmetics are the vegetal or naturally occurring phospholipids, such as those obtained from soy or from bovine or swine cutis or brain, similar to the ones that are found in human dermis; for other uses, a phospholipid that is chemically homogeneous and defined in its structure units (acyl and phosphoryl amine group) is preferred.

The complex compounds according to the invention are prepared by reacting a flavonoid in an aprotic solvent with the phospholipid dissolved in the same solvent. The mole ratio of phospholipid to flavonoid is in the range from 0.5 to 2; a more preferable mole ratio being about 1. After solubilization has been completed, the complex compound is isolated by removing the solvent under vacuum, by lyophilization or by precipitation with nonsolvents.

The complex compound thus obtained is lipophile in character and is soluble in nonpolar and aprotic solvents in which the individual components of the complex compound are normally insoluble.

The formation of a molecular complex is confirmed by a NMR spectroscopy study of the proton, carbon-13 and phosphorus, by comparing the spectra of the individual constituents with those of the reaction product. In the complex's $^1$H-NMR spectrum, the signals of the protons characteristics of the flavonoid molecule are not detectable, or are very enlarged, whereas the protons belonging to the lipid can be observed. Clearly apparent in the same spectrum is a broadening of the band of N-(Me)$_3$ group of choline, showing that this moiety is involved in the complex formation.

In the $^{13}$C-NMR spectrum, the value of the relaxation times of the nuclei that are most involved in the complex's formation is reduced in a similar manner to the proton spectrum, until disappearance of all the signals of the flavonoid and the choline and glyceric residue of the phospholipid takes place. In the $^{31}$P-NMR spectrum, a substantial broadening of the phosphorus band is observed with conspicuous peak shift.

On the basis of the spectroscopic results, in the formation of these complexes the polar head of the phospholipid is involved while the fatty acid moieties retain a high degree of mobility conferring marked lipophilia at the new molecule.

It has also been found that the formation of the complexes with phospholipids can advantageously be utilized for the extraction and purification of flavonoids from total or purified extracts prepared from plants that are of interest in the pharmaceutical and cosmetic fields.

Thus, the invention also provides a process for purifying flavonoids from plants, such for example as Gingko biloba, Crataegus sp., Passiflora incarnata, Tormentilla potentilla, Tea sinensis.. Aurantium sp., Citrus sp., Eucaliptus sp., Matricaria chamomilla, Fagara sy-

*lanthoides*, and plants containing luteolin glucosides, these latter being particularly useful for use in cosmetics as will be shown further.

When operating on extracts, it is convenient to use dry extracts which are treated with phospholipids dissolved in the reaction solvent (usually chlorinated solvents or dioxane); the flavonoid substances go into solution following complexation and the various constituents of different nature, present in the extracts, can be removed by filtration. The solution containing the desired products may, after concentration, be dried directly or precipitated in a nonsolvent for removing excess phospholipid. Complexes with other polyphenol substances can also be obtained by treating aqueous or hydroalcoholic extracts, in the same extraction medium, with phospholipids; the complexes of the polyphenolic substances are obtained, by operating with excess phospholipid, as precipitates that can be separated from the extract by filtration or centrifugation; the precipitate may be redissolved in aprotic solvent and reprecipitated, after dehydration, in nonsolvents for the removal of lipid in excess.

The complex compounds of the invention, as obtained from the pure compounds or the extracts, possess higher bio-availability, for instance the complexes by topical application, are 2 to 4 times as active as are the substances administered in a free form.

As it is apparent from Table I, in which the vasodilatory activity of the *Gingko biloba* extract is compared peculiar action of the flavonoids in general, and of the catechuic derivatives in particular, is their fibroblastic proliferation stimulating action, which action is equally useful in dermatology for ulcer healing and in cosmetic treatments where it intervenes to increase the synthesis of the mucopolysaccharides and of the collagen in the derma perivascular connective tissue.

Still in with the cosmetics field, glucosidate derivative of luteolin and the *Gingko biloba* extract itself, when in complexed forms, have proved useful in bleaching melaninic freckles or pigmented maculae occuring in senescent skin, or as caused by exposure to the sun, the use of contraceptives, etc . . . Surprisingly, the complexed form remains a longer time in the skin to go deeper into it so that the effect is more apparent and is faster than with the free from. With other flavonoids, such as apigenin and its derivatives and luteolin and its glucosides, the anti-inflammatory activity, following topical application (already known in literature), measured as carragenin oedema-inhibition and in terms of UV radiation protection, was in all cases higher in the complex compounds of the invention than in the free flavonoids.

Quercetin, apigenin and the corresponding phosphatidylcholine-complexes, have been tested for effectiveness in inhibiting the Croton oil oedema. From the results given in Table III it clearly appears that the complexed forms are higher in activity than the free flavonoids.

TABLE 1

| | | | | Arterial pressure in rat in state of spontaneous hypertension | | | | | | |
|---|---|---|---|---|---|---|---|---|---|---|
| | Dose | No. | | Systolic pressure, mm/Hg | | | | | | |
| | mg/ | ani- | Basal | 4 h | 24 h | 4 h | 24 h | 4 h | 24 h | 4 h | 24 h |
| Substance | kg | mals | pressure | I Die | | II Die | | III Die | | IV Die | |
| Controls | | 7 | 206 ± 5 | 203 ± 6 | 204 ± 5 | 200 ± 6 | 203 ± 4 | 199 ± 5 | 199 ± 6 | 199 ± 6 | |
| Gingko biloba extract | 5 | 7 | 209 ± 4 | 199 ± 6 (−7) | 196 ± 5 (−10) | 190 ± 7 (−16) | 189 ± 2* (−14) | 196 ± 4* (−10) | 189 ± 5** (−17) | 183 ± 3*** (−23) | |
| Gingko biloba/phosphatidyl choline complex | 12,5 | 7 | 206 ± 3 | 191 ± 5** (−18) | 187 ± 5** (−22) | 186 ± 8** (−23) | 184 ± 7** (−24) | 181 ± 7** (−28) | 180 ± 3*** (−29) | 177 ± 4*** (−32) | |

*p lower than 0.05
**p lower than 0.01
***p lower than 0.001 with that of the corresponding complex compound, absorption in a rat under genetic hypertension is more favourable for the complexed form; the same results are obtainable in the activity on the microcircle and the platelet aggregation and in tests connected with topical application.

Table II gives data concerning the antiedematous activity exhibited by the *Gingko biloba* extract both alone and in complexed form, in croton oil test by topical application. It clearly appears from these data that the complexed form has substantially higher activity than normal one.

Moreover, of particular interest in the specific case of the extracts from *Gingko biloba, Crataegus* and *Passiflora incarnata,* is the increment of the blood flow at the cutaneous microcircle level, that can be caused to occur in application areas of respective complexed forms, as compared with free forms; here, the action of the complexed form, besides being higher in intensity at the same dose of active principle, is longer lasting in time. It can be easily appreciated how an increment in blood flow at the cutaneous level is of importance also in cosmetic applications, in order to maintain the skin moisturised, elastic and in physiological conditions. A

TABLE 2

| Inhibition of the Croton oil oedema in mouse. | | | | |
|---|---|---|---|---|
| Substances | Dose μg | Animals No. | Edema mg ± E.S. | Reduction % |
| Controls | — | 8 | 5,6 ± 0,4 | — |
| Gingko biloba extract | 300 | 8 | 4,7 ± 0,9 | −16 |
| Gingko biloba/phosphatidyl choline complex | 75 | 8 | 0,8 ± 0,3* | −86* |

*p ≦ 0,001

TABLE 3

| inhibition of Croton oil oedema in mouse | | | | |
|---|---|---|---|---|
| Substances | Dose ug | Animals No. | Edema mg ± E.S. | Reduction % |
| Controls | — | 8 | 5,6 ± 0,4 | |
| Quercetin | 50 | 8 | 4,2 ± 0,6 | −25 |
| Apygenin | 30 | 8 | 3,4 ± 0,5 | −39 |
| Quercetin/phosphatidyl choline complex | 35 | 8 | 3,0 ± 0,6 | −47 |
| Quercetin/phosphatidyl choline complex | 70 | 8 | 1,5 ± 0,4 | −73 |
| Apygenin/phosphati- | 70 | 8 | 0.8 ± 0.3 | −86 |

TABLE 3-continued

| | inhibition of Croton oil oedema in mouse | | | |
|---|---|---|---|---|
| Substances | Dose ug | Animals No. | Edema mg ± E.S. | Reduction % |
| dyl choline complex | | | | |

The epithelium-repairing activity and the fibroblastic proliferation-stimulating activity exhibited by the phospholipid complexes of catechuic dimeric and trimeric substances, such as those isolated from Tormentilla, are significantly greater than in the case with the free forms.

The peculiar activities of flavones, such as their capillary-protective and vasotropal activities, have been checked for the complex compounds of rutin, diosmin, quercetin and of flavonoids from whitethorn, passion flower and *Gingko biloba*.

Especially when tested by topical application, the complexes of the above-mentioned products have shown to provide significant protective effect. From an applicative point of view of pharmaceutical and cosmetic technology, the various complex compounds obtained as above can be employed as microdispersions in water by preparing them by homogenization using high-speed stirrers or ultrasonic procedures, or they may be incorporated as such into appropriate pharmaceutical or cosmetic preparations. The complexes are always provided in solid form thereby enabling them to be used for preparing tablets, capsules, powders, suppositories, creams and gels, or in aqueous microdispersions that are conveniently kept in dispersed state with thickening agents. Advantageously, in view of the higher activity exhibited by the complexed forms according to the invention, the dosage of the active principle may, under certain circumstances, be decreased while maintaining the specific activity unchanged.

Suitable forms for pharmaceutical and/or cosmetic uses by topical application, are creams, gels or aqueous microdispersions containing 0.1 to 10% by weight of one or more complex compounds of the invention. Said forms will be administered once or several times daily, depending on the contemplated use. Suitable forms for pharmaceutical uses, by oral or parenteral administration, are tablets, capsules, syrups, granules, solutions and suspensions which contain unit doses of the complexate active principle in the range from 1 to 500 mg. Said pharmaceutical forms will be administered once or several times a day, depending on the severity of the pathology to be treated and the patient conditions. The compositions according to the invention can in particular be used for treating states of inflammation, of altered platelet aggregation states, of altered capillary fragility and permeability and, in general, in all the fields in which an activity of the flavonoids is recognized at present.

In the following examples, that are given for illustrative purposes and not to be constructed as limiting the invention, use has been made of a soy phosphatidylcholine containing, on an average, as fatty acids: 63% linoleic acid, 16% palmitic acid, 3.5% stearic acid and 11% oleic acid based on the total acids, or natural mixture of phospholipids extracted from vegetal sources.

EXAMPLE 1

Preparation of quercetin/di-stearoyl phosphatidylcholine equimolecular complex 3.02 g of quercetin were suspended in 100 ml of methylene chloride; 8 g of distearoyl phosphatidylcholine were added to the suspension and the mixture was heated to mild reflux to complete dissolution. The solution was concentrated to a volume of 20 ml, then diluted with .200 ml of n-hexane, under stirring. The precipitated product was filtered and dried under vacuum at 40° C. 10.6 g of a yellow powder were obtained, having $E_{1\%}=143.6$ at 258 nm (CHCl$_3$); $E_{1\%}=116.3$ at 362 nm (CHCl$_3$).

EXAMPLE 2

Preparation of quercetin-3-galactoside/soy phosphatidylcholine equimolecular complex 4.64 g of quercetin-3-galactoside (hyperoside) were dissolved in 150 ml of a dioxane-ethanol 2:1 mixture, in the presence of 7.8 g of soy phosphatidylcholine (titre 95%). When the solution was clear, ethanol was removed by distillation under vacuum at 40° C., and the dioxane solution was freeze-dried.

12.1 g of a straw yellow powder, completely soluble in chloroformethyl ether, were obtained. The product showed no signals at $^1$H-NMR (CDCl$_3$) which could be assigned to aromatic protons and to those of the saccharidic moiety.

$E_{1\%}$ in CHCl$_3$ of 160.2 at 258 nm.

EXAMPLE 3

Preparation of quercetin-3-rhamnoglycoside/soy phosphati dyl-choline complex 6.1 g of quercetin-3-rhamnoglycoside were dissolved together with 15.60 g (0.02 mole) of soy phosphatidylcholine (95% titre) in 500 ml of dioxane, heating the mixture to mild reflux for 10 minutes. When dissolution was complete, the mixture was cooled and concentrated to 40 ml under vacuum. The concentrate was poured into 500 ml of n-hexane and the resulting precipitate was filtered under vacuum, washing thoroughly with n-hexane. After drying, 20.2 g of the complex were obtained, having: m.p.=107–109° C.; $E_{1\%}=90.4$ at 260 nm and 72.7 at 367 nm; $[\alpha]_D^{20}+10.1°$ (C=1% in CHCl$_3$).

EXAMPLE 4

Preparation of kaempferol-3-glycoside/soy phosphatidylcholine 4.48 g of kaempferol-3-glycoside and 7.8 g of soy phosphatidylcholine were dissolved in 60 ml of dioxane. The obtained solution was freeze-dried. 12 g of the complex were obtained, which was completely soluble in aprotic solvents, and had NMR spectra in agreement with those of complexated flavonoid products. The products had $E_{1\%}$ in CHCl$_3=158.5$ at 260 nm.

EXAMPLE 5

Preparation of vitexine-2''-rhamnosyde-2''-acetate/soy phosphatidylcholine complex 3.2 g of vitexine-2''-rhamnosyde-2''-acetate and 3.9 g of phosphatidylcholine were dissolved in 30 ml of a dioxane:ethanol 5:1 mixture, then freeze-dried. 7 g of a light yellow powder were obtained, having $E_{1\%}=116.9$ at 272 nm (CHCl$_3$); $E_{1\%}=130.5$ at 330 nm (CHCl$_3$);

and spectroscopic data in agreement.

EXAMPLE 6

Preparation of *Ginkgo biloba* extract/soy phosphatidylcholine complex 10 g of *Ginkgo biloba* extract, having average titre in Ginkgo flavone-glycosides of about 25%, and 15 g of soy phosphatidylcholine (95% tit.) were dissolved in 200 ml of a mixture of 6 parts of methylene chloride and 1 part of methanol. When dissolution was complete, the solvent was distilled off under vacuum to small volume; the residue was diluted with 200 ml more of methylene chloride, filtering any turbidity.

Solvent was evaporated to small volume; the mixture was diluted with 300 ml of n-hexane and the product precipitated in form of a light beige solid, which was dried at 40° C. under vacuum. 22 g of product were obtained, which was completely soluble in apolar solvents; the extract was in form of a complex, as evidenced by the NMR spectra, which showed no signals of aromatic protons from flavonoid compounds. Said extract may be directly used for microdispersion or incorporation into pharmaceutical formulations.

EXAMPLE 7

Preparation of apigenin/soy phosphatidylethanolamine complex 2.7 g of apigenin and 6.9 g of soy phosphatidylethanolamine (96 % tit.) were dissolved in 80 ml of methylene chloride. When dissolution was complete, methylene chloride was evaporated off to small volume, and the mixture was precipitated with 200 ml of n-hexane. The precipitated product was filtered and dried under vacuum at 40° C.

8.2 g straw yellow product were obtained, having spectroscopic characteristics in agreement with the described complexes.

EXAMPLE 8

Preparation of apigenin/distearoylphosphatidylcholine complex 2.7 g of apigenin were suspended in 100 ml of a dioxane:methanol 7:3 mixture, added with 8 g of distearoylphosphatidylcholine, and heated to reflux to complete dissolution.

The obtained solution was concentrated to dryness, the residue was dissolved in 50 ml of chloroform-methanol 9:1. The chloroform solution was evaporated to small volume and the residue was poured into 100 ml of n-hexane. 9 g of the complex were obtained, having the following characteristics: m.p. 150° C.;

$E_{1\%}=164.6$ at 270 nm; $E_{1\%}=156.2$ at 324 nm.

EXAMPLE 9

Preparation of luteolin 7 glycoside/soy phosphatidyl choline complex 2.24 g of luteolin-7-glucoside were suspended in 100 ml in a dioxane-methanol 7:3 mixture, and treated with 4 g of soy phosphatidylcholine (95% tit.); the mixture was refluxed till complete dissolution; solvent was removed under vacuum and the residue was taken up in 50 ml a chloroform-methanol 8:3 mixture, which was subsequently removed. The residue was dissolved in 100 ml of methylene chloride. After concentration to small volume, the residue was poured into 100 ml of n-hexane. 6.2 g of luteolin-7-glycoside and soy phosphatidylcholine complex were obtained, having the following characteristics: m.p. 120-130° C.; $E_{1\%}$ in $CHCl_3$ 113.89 at 258 nm.

EXAMPLE 10

Preparation of diosmin/soy phosphatidylcholine complex 6 g of diosmin and 15.5 g of soy phosphatidylcholine (95% tit.) were suspended in a dioxane-methanol 7:3 mixture, and refluxed to complete dissolution. The solution was concentrated under vacuum to small volume and the residue was redissolved in methylene chloride. After evaporation of the solution, 21 g of diosmin-phosphatidylcholine complex were obtained, having chemico-physical and spectroscopic characteristics in agreement with those of the above described complexes.

EXAMPLE 11

Preparation of *gingko biloba* depurated extract/total soy phospholipids complex 10 g of *Gingko biloba* depurated extract having titre=24% in Gingkoflavoneglycosides in 100 ml of methylene chloride were added with 15 g of soy phospholipids, having phosphatidylcholine content: 30%, phosphatidylethanolamine content: 20%; phosphatidylinositole content: 6% + minor phospholipids, in 15 ml of methanol, under stirring.

When the solution was clear, solvent was removed under vacuum and the residue was dissolved in 50 ml of chloroform; the solution was then poured into 500 ml of n-hexane, under strong stirring.

A viscous precipitate was obtained, which was decanted and dried under vacuum at 50° C., for 12 hours.

A yellow-beige powder was obtained, having m.p. 105° C., and chemico-physical and spectroscopic characteristics corresponding to a complex.

EXAMPLE 12

Preparation of Hawthorn/soy phosphatidylcholine complex 10 g of Crataegus sp. extract, prepared starting from blossomed tops, containing 20% of flavonoidic substances expressed as hyperoside, were suspended together with 20 g of soy phosphatidylcholine (95% tit.) in 300 ml of a 9:1 chloroform-methanol mixture. When the solution was complete, the solvent was evaporated and the residue taken up with 300 ml of methylene chloride. The solvent was completely removed under vacuum.

A beige solid, having spectroscopical characteristics confirming the complex formation and easily soluble in water, was obtained.

EXAMPLE 13

Cream containing as the active ingredient the complex of Example 11

| Formulation for 100 g of cream | |
|---|---|
| Gingko biloba complex (Ex. 11) | 2.5 g |
| Carboxyvinylpolymer (Carbomer 934 ®) | 1.2 g |
| 30% Sodium laurylsarcosinate | 0.5 g |
| Imidazolidinylurea | 0.3 g |
| Triton ® 80 | 0.1 g |
| Polysorbate 80 | 3 g |
| Hydrogenated lanoline | 5 g |
| Spermacetes | 5 g |
| Polyisoprene | 5 g |
| Wheat oil | 2 g |

-continued

| Formulation for 100 g of cream | |
|---|---|
| Dimethylsilyconic oil | 0.5 g |
| 10% Sodium hydroxide sol. | 2 g |
| Perfum | 0.3 g |
| Water | q.s. to 100 g |

EXAMPLE 14

Oleolyte containing as the active ingredient the complex of Example 11.

| Formulation for 100 g of oleolyte | |
|---|---|
| Gingko biloba complex (Ex. 11) | 2.5 g |
| Softigen ® 727 | 70 g |
| (C$_8$-C$_{12}$ ethoxylated triglycerides) | |
| Volpo ® 20 (polyoxyethylene 20 oleylether) | 7 g |
| Isopropylmiristate | 20 g |
| Preservants | 0.2 g |
| Perfum | 0.3 g |

EXAMPLE 15

Lotion containing as the active ingredient the complex of Example 11

| Formulation for 100 g of lotion | |
|---|---|
| Gingko biloba complex | 2.5 g |
| Softigen ® 727 | 25 g |
| (C$_8$-C$_{12}$ ethoxylated triglycerides) | |
| Imidazolidinylurea | 0.3 g |
| Octilinone | 0.1 g |
| Volpo ® 20 (polyoxyethylene 20 oleylether) | 7 g |
| 2,5% Parfumed composition | 1 g |
| Depurated water | q.s. to 100 g |

EXAMPLE 16

Gel containing as the active ingredient the complex of Example 11

| Formulation for 100 g of gel | |
|---|---|
| Gingko biloba complex | 2.5 g |
| Softigen ® 727 | 25 g |
| (C$_8$-C$_{12}$ ethoxylated triglycerides) | |
| Imidazolidinylurea | 0.3 g |
| Octilinone | 0.1 g |
| Volpo ® 20 (polyoxyethylene 20 oleylether) | 7 g |
| Carboxypolymethylene (Carbopol ® 934) | 1.5 g |
| Triethanolamine | 2 g |
| 2.5% Parfum | 1 g |
| Depurated water | q.s. to 100 g pH 7-7.2. |

EXAMPLE 17

Capsules containing as the active ingredient the complex of Example 6

| Formulation for capsules containing 50 mg of complex | |
|---|---|
| Gingko biloba complex | 50 mg |
| Silica powder | 30 mg |
| Insoluble crosslinked polyvinylpirrolidone | 30 mg |
| Mais starch | 20 mg |
| Sodium carboxymethylcellulose | 10 mg |
| Polyvinylpirrolidone 30000 PM | 7 mg |
| Magnesium stearate | 3 mg |

EXAMPLE 18

Capsules containing as the active ingredient the complex of Example 12

| Formulation for capsules containing 150 mg of complex | |
|---|---|
| Hawthorn complex | 150 mg |
| Silica powder | 60 mg |
| Mais starch | 20 mg |
| Sodium carboxymethylcellulose | 10 mg |
| Lactose | 30 mg |
| Magnesium stearate | 3 mg |

EXAMPLE 19

Cream containing as the active ingredient the complex of Example 7

| Formulation for 100 g of cream | |
|---|---|
| Apigenin complex | 2.0 g |
| Polyethyleneglycol | 2 g |
| Polysorbate 80 | 3 g |
| Cetyl alcohol | 10 g |
| Wheat oil | 2 g |
| Silicon oil 350 cps | 0.5 g |
| Antioxidants (oxinex 2004) | 0.1 g |
| Carboxyvinylpolymer (Carbomer 934 ®) | 0.8 g |
| Triethanolamine | 1.2 g |
| Preservants (a mixture of methyl and propyl p-hydroxybenzoates) | 0.2 g |
| Parfumed composition | 0.1 g |
| Depurated water | q.s. to 100 g |

EXAMPLE 20

Cream containing as the active ingredient the complex of Example 9

| Formulation for 100 g of cream | |
|---|---|
| Luteoline complex | 1.5 g |
| Glycerol monostearate | 3 g |
| C$_8$-C$_{12}$ Liquid saturated triglycerides | 10 g |
| Cetyl alcohol | 4 g |
| Hydrogenated lanoline | 10 g |
| Pentamethyleritrene | 3 g |
| Polysorbate 80 | 10 g |
| Carboxyvinylpolymer (Carbomer 934 ®) | 0.5 g |
| Triethanolamine | 0.6 g |
| Parfumed composition | 0.2 g |
| Preservants (a mixture of methyl and propyl p-hydroxybenzoates) | 0.2 g |
| Depurated water | q.s. to 100 g |

EXAMPLE 21

Gel containing as the active ingredient the complex of Rutine

| Formulation for 100 g of gel | |
|---|---|
| Rutine complex | 1 g |
| Imidazolidinylurea | 0.3 g |
| Octilinone | 0.1 g |
| C$_8$-C$_{12}$ Ethoxylated triglycerides (Softigen 767) | 25 g |
| Polyoxyethylene 20 oleylether | 5 g |
| Carboxyvinylpolymer (Carbomer 934) | 1.5 g |
| Triethanolamine | 2 g |
| Parfumed composition | 0.1 g |
| Depurated water | 65 g |

EXAMPLE 22

Cream containing as the active ingredient the complex of Rutine

| Formulation for 100 g of cream | |
|---|---|
| Rutine complex | 2 g |
| Isopropyl miristate | 10 g |
| 30% Sodium laurylsarcosinate | 3 g |
| Carboxyvinylpolymer (Carbomer 934 ®) | 1 g |
| 10% Sodium hydroxide solution | 2.2 g |
| Preservants (methyl and propyl p-hydroxybenzoates) | 0.2 g |
| Lavender essences | 0.2 g |
| Depurated water | q.s. to 100 g |

EXAMPLE 23

Solution containing as the active ingredient the complex of Rutine

| Formulation for 100 g of solution | |
|---|---|
| Rutine complex | 1 g |
| Imidazolidinylurea | 0.3 g |
| Octilinone | 0.1 g |
| Glycerides PEG-6-caprilic/capric | 25 g |
| Polyoxyethtlene 20 oleylether | 5 g |
| Parfumed composition | 0.1 g |
| Water | q.s. to 100 g |

We claim:

1. A complex of a flavonoid with a phospholipid wherein the flavonoid is a member selected from the group consisting of quercetin, kaempferol, quercetin-3-ramnoglucoside, quercetin-3-ramnoside, quercetin-3-glucoside, hyperoside, (+) apigenin, apigenin-7-glucoside, luteolin, luteolin-glucoside ramnoglucoside, 5,7,3',4'-pentahydroxy-flavone-3D-alfa-rhamnopyranosyl-4-D-beta-O-(6''-transcoumaroyl-)glucopyranoside, 3,4,5,4'-tetrahydroxy-flavone-3-D-alfa-rhamnopyranosyl-4-D-beta-O-(6''-trans-coumaroyl-)glucopyranoside, Ginkgonetine, Isoginkgonetine, Sciedopitasine, rutine and Bilobetine, and the phospholipid is a member selected from the group consisting of soy lecithins, egg lecithin phospholipids from bovine or swine brain or dermis, phosphatidyl choline, phosphatidyl serine, phosphatidyl ethanolamine in which the acyl groups are the same or different and are derived from palmitic, stearic, oleic, linoleic, linolenic acid, and wherein the phospholipid to flavonoid ratio is in the molar range from 0.5 to 2M.

2. The complex according to claim 1 which is the quercetin/di-stearoyl phosphatidylcholine equimolecular complex.

3. The complex according to claim 1 which is the quercetin-3-galactoside/soy phosphatidylcholine equimolecular complex.

4. The complex according to claim 1 which is the quercetin-3-rhamnoglycoside/soy hosphatidylcholine complex.

5. The complex according to claim 1 which is the kaempferol-3-glycoside/soy phosphatidylcholine.

6. The complex according to claim 1 which is the vitexine-2''-rhamnoside-2''-acetate/soy phosphatidylcholine complex.

7. The complex according to claim 1 which is the *Ginkgo biloba* extract/soy phosphatidylcholine complex.

8. The complex according to claim 1 which is the apigenin/soy phosphatidylethanolamine complex.

9. The complex according to claim 1 which is apigenin/distearoylphosphatidylcholine complex.

10. The complex according to claim 1 which is luteolin-7-glycoside/soy phosphatidylcholine complex.

11. The complex according to claim 1 which is diosmin/soy phosphatidylcholine complex.

12. The complex according to claim 1 which is *Gingko biloba* depurated extract/total soy phospholipids complex.

13. The complex according to claim 1 which is Hawthorn/soy phosphatidylcholine complex.

14. A cosmetic composition for topical application containing 0.1–10% by weight as the active principle or a complex according to claim 13 in the form of a solution, powder, cream, gel, or as an aqueous microdispersion, with pharmaceutically acceptable carriers.

15. The composition according to claim 14 wherein said active principle is the *Gingko biloba* depurated extract/total soy phospholipids complex.

16. The composition according to claim 14 wherein the active principle is luteolin-7-glycoside/soy phosphatidylcholine complex.

17. The composition according to claim 14 wherein the active principle is luteolin-7-glycoside/soy phosphatidylcroline complex.

18. The composition according to claim 14 wherein the active principle is a phospholipid complex from luteolin or rutin.

* * * * *